United States Patent [19]

Hall et al.

[11] 4,243,597
[45] Jan. 6, 1981

[54] VOLATILE URANYL COMPOUNDS

[75] Inventors: Richard B. Hall, Clark; Andrew Kaldor, Watchung; George M. Kramer, Berkeley Heights, all of N.J.; Martin B. Dines, Santa Ana, Calif.

[73] Assignee: Exxon Research & Engineering Co., Florham Park, N.J.

[21] Appl. No.: 961,363

[22] Filed: Nov. 16, 1978

Related U.S. Application Data

[63] Continuation-in-part of Ser. No. 868,450, Jan. 10, 1978, abandoned, which is a continuation of Ser. No. 751,901, Dec. 17, 1976, abandoned.

[51] Int. Cl.³ .................... C07D 307/12; C07F 5/00
[52] U.S. Cl. ..................... 260/347.8; 204/DIG. 11; 260/429.1; 260/704; 260/706
[58] Field of Search ................... 260/429.1, 347.8; 204/157.1 R, DIG. 11

[56] References Cited

PUBLICATIONS

Casellato et al., Inorg. Chimica Acta, vol. 18, pp. 84 to 86 (1976).
Subramanian et al., J. Inorg. Nucl. Chem., vol. 33, pp. 3001 to 3009 (1971).

Primary Examiner—Leland A. Sebastian
Attorney, Agent, or Firm—A. H. Krumholz; V. A. Slabey

[57] ABSTRACT

Novel compositions of matter are disclosed having the formula $UO_2AA'L_n$, wherein n is 0 or 1, and in which A and A' are anions whose conjugate acids have boiling points less than about 200° C. and $pK_a$ values of 4.8 or less, L is a neutral ligand having a boiling point less than about 190° C. and having an equilibrium constant for the exchange reaction with tetrahydrofuran of between about $10^{-3}$ and $10^3$, and the combination of A, A' and L satisfy five or six coordination sites of the central uranium atom.

14 Claims, 1 Drawing Figure

*K BEING THE EQUILIBRIUM CONSTANT FOR THE REACTION

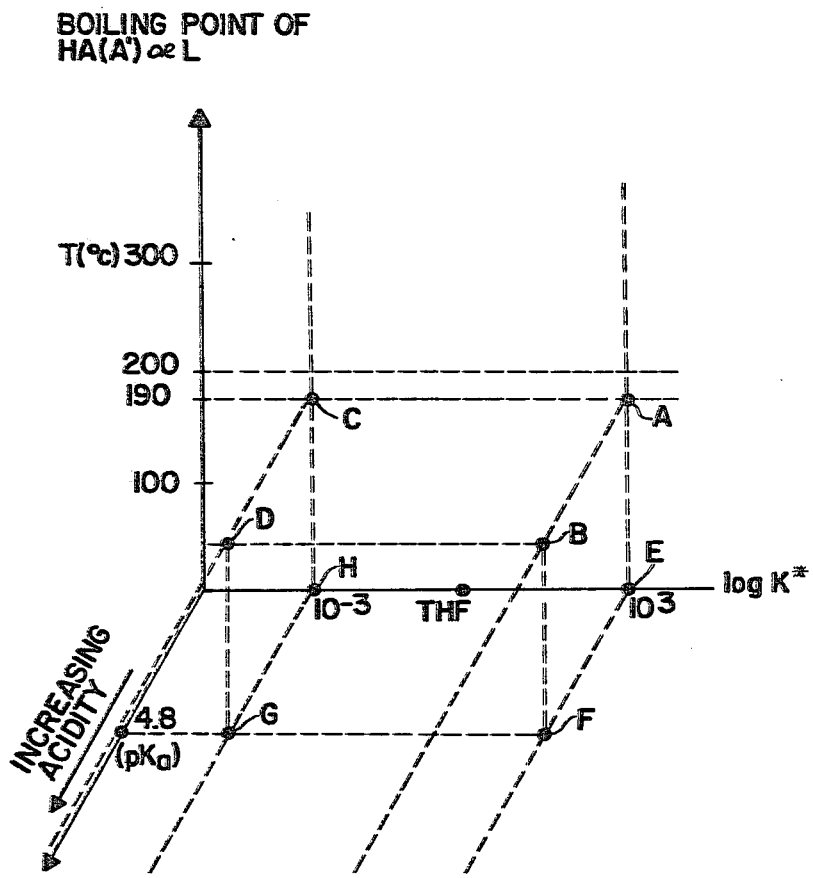
*K BEING THE EQUILIBRIUM CONSTANT FOR THE REACTION
$$UO_2[(CF_3CO)_2CH]_2 \cdot THF + B \underset{HCCl_3}{\overset{K}{\rightleftharpoons}} UO_2[(CF_3CO)_2CH]_2 \cdot B + THF$$

VOLATILE URANYL COMPOUNDS

CROSS-REFERENCE TO RELATED APPLICATIONS

This application is a Continuation-In-Part of application Ser. No. 868,450, filed on Jan. 10, 1978, now abandoned which is a continuation of application Ser. No. 751,901, filed on Dec. 17, 1976 also now abandoned.

BACKGROUND OF THE INVENTION

The present invention relates to a composition of matter containing the uranyl ion. More specifically, the present invention relates to such compositions of matter which are useful in uranium isotope separation processes.

The significance of the present invention resides primarily in the fact that the discovery of such volatile uranyl compounds permits their use for the separation of isotopes, as is disclosed in copending application Ser. No. 865,963, filed on Dec. 30, 1977, and assigned to Exxon Research and Engineering Company, the assignee of the present application. The compounds of the present application are volatile uranyl ion containing compounds which have an isotopically shifted infrared absorption spectrum associated therewith, and which therefore can be used to separate isotopes by vaporizing the subject compound and irradiating same with infrared radiation which is preferentially absorbed by a molecular vibration of molecules therein containing a predetermined isotope of the element to be separated. This provides excited molecules of this compound enriched in the molecules of the compound containing that predetermined isotope, thus enabling separation of those excited molecules. In addition, these particular molecules exhibit a number of properties which render them particularly useful in such processes, such as an isotopic shift within the range of wavelengths of from about 810 to 1116 cm$^{-1}$, i.e. within the range of commercially available $CO_2$ lasers, and they exhibit relatively high vapor pressures at relatively low temperatures.

U.S. Pat. No. 3,951,768, which was issued on Apr. 8, 1976 to Carl Gurs on an application filed before the effective date hereof, discusses the use of a $CO_2$ laser for the separation of isotopes, and mentions as a specific compound therein $UO_2(NO_3)_2.6H_2O$ along with a number of other compounds as possibly being useful for the separation of uranium isotopes. This patent thus appears to suggest the use of uranyl compounds with a $CO_2$ laser for isotope separation, however it should be noted that since the compound listed in the Gurs' patent is listed along with others which do not readily absorb light from the $CO_2$ laser, it is not clear what was exactly intended to be taught therein. Nevertheless, a uranyl compound is mentioned. The specific compound in question, however, is believed to be non-volatile in the sense that it decomposes and therefore cannot be employed in the vapor phase for isotope separation. In fact, most uranyl compounds decompose without vaporization when heated, and it is this fact which renders the invention of the compounds of the present invention, which possess such volatility, of such significance.

With further regard to the compounds of the present invention, early reports on uranyl-containing compounds were made by Messrs. Schlessinger and Brown in the late 1940's. Thus, in U.S. patent application Ser. No. 662,600 published in the Official Gazette on Mar. 6, 1951, Chemical Abstract 46, 10192b, those authors disclose a class of uranyl-containing β-diketone compounds which they investigated in connection with vapor phase processes for gas diffusion and uranium ore separation. They thus disclose compounds having a general formula as follows:

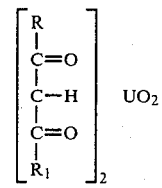

where R may be a fluoro substituted alkyl group and $R_1$ a halogen substituted radical. Subsequently, however, these same individuals, in the Journal of the American Chemical Society, 75, pages 2446–8 (1953) went on to report that "there is little likelihood of finding such compounds having vapor tensions above 0.1 mm. at 130°." In that article the only vapor pressure reported by the authors for a β-diketone (in this case for $UO_2$ (1,1,1-trifluoroacetylacetone)$_2$ was 0.0027 torr at 130° C.

These articles, in addition to several other articles, do discuss the relationship between increased volatility and fluorination. Messrs. Schlessinger and Brown, for example, discuss the increase in volatility achieved by replacement of the methyl radicals of acetylacetone by the trifluoromethyl group. They conclude, however, that based on their observations the search for a significantly more volatile uranium compound of the diketone type "held little promise of success."

One uranyl ion-containing compound which has been reported, although sparsely, is uranyl hexafluoroacetylacetonate,

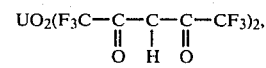

$UO_2(hfacac)_2$ and its complexes. Belford et al (J. Inorg. Nucl. Chem. 14, 169 (1960) first prepared and described a "tetrahydrate" which presumably (no formula is given in the reference) is $UO_2(hfacac)_2.4H_2O$, and which decomposes above 58° C. In this article the authors show the infrared absorption bands for various uranyl compounds, and discuss the effect of ligand substitution on the visible spectra. The authors thus conclude that the more basic ligands attach more securely to the uranium atom, decreasing its coordinating tendency.

Hfacac, which is a chelating anion, is known to stabilize metal salts and allow for volatile species (Kutal, J. Chem. Ed. 52. 319 (1975)). Furthermore, this anion has no bands in the infrared region of 900–1000 cm$^{-1}$, the region where the $UO_2^{+2}$ group has a strong antisymmetric stretching mode, which is of interest for any isotope selective $CO_2$ laser irradiation.

In general, uranyl compounds can have five or six atoms coordinated to the central U ion (in addition to the oxygens of the uranyl), but preferably five such atoms. Where the hfacac anion is utilized, each hfacac group uses two coordination sites, and thus in the case of the preferred configuration with five atoms coordinated to the central U atom, this leaves one open site for a neutral ligand which is necessary to produce a stable uranyl containing vapor. In the absence of an appropriate stabilizing neutral ligand it is impossible in this case to generate the stable monomeric vapor of the uranyl (hfacac)$_2$. The Belford et al paper described above shows that water molecules are not suitable as neutral ligands since the compound does not volatilize intact so as to form such a stable vapor phase species.

If no other molecules are present, UO$_2$(hfacac)$_2$ will dimerize, sharing two of the oxygens, and thus each UO$_2^{+2}$ ion will have the requisite five oxygens around it. This dimer is not desired for laser isotope separations (monomers are preferred) because its volatility is too low and it allows for scrambling of absorbed energy and reduction in selectivity. Energy absorbed by the selectively excited UO$_2^{+2}$ group is diluted due to enhanced transfer to the second UO$_2^{+2}$ group which is intimately bound to it in a dimer or oligomer. Therefore, judicious selection must be made to choose a neutral Lewis base molecule to stabilize the uranyl (hfacac)$_2$ as a monomer, to confer high volatility, and to have no infrared bands which might interfere with the UO$_2^{+2}$ asbsorption. In addition, the presence of this neutral ligand may also enhance any subsequent photochemical reaction desirable in an isotopic selective process.

There have been reports of UO$_2$(hfacac)$_2$.L compounds in which L=aromatic amine oxides (Subramanian et al, Journal Inorg. Nucl. Chem. 33, 3001 (1971)), phosphine oxides and sulfoxides (Sieck, Gas Chromatography of Mixed-Ligand Complexes of the Lanthanides and Related Elements, Ph.D. Thesis, Iowa State Univ., 1971)). However, while the Subramanian et al article discusses compounds such as pyridine N-oxide as such a ligand, there is no discussion of the volatility of such compounds, and the article further indicates that the amine N-oxides were selected by the authors over such materials as alcohols, ethers and amines because of the more polar nature of these compounds and the search for a stronger bond therewith. In addition, the Sieck thesis, as well as two other articles by Sieck in Chemical Abstracts, 75, 147395Q and at Nuclear Science Abstracts, 25 (17), 39410 (1971), include discussions regarding the use of these mixed ligand complexes for the separation and detection of UO$_2^{+2}$, and mention is made of the detection of these complexes by gas chromatography at column temperatures of about 200° C.

Mitchell (Synergic Solvent Extraction and Thermal Studies of Fluorinated Beta-Diketone-Organophosphorus Adduct Complexes of Lanthanide and Related Elements, Ph.D. Thesis Iowa State Univ., 1970) prepared the tributylphosphate complex of UO$_2$(hfacac)$_2$ and showed that it sublimed at about 150° C. But, as discussed above, significant vapor pressure at lower temperatures is desired in an isotope separation process and a sublimation temperature below about 130° C. or even near or less than 100° C. is much preferred.

Very recently a comprehensive review of the complex chemistry of a number of uranyl compounds with various chelating ligands appeared in which the paucity of work on UO$_2$(hfacac)$_2$ and its complexes was evident (Casellato et al, Inorg. Chimica Acta, 18, 77 (1976)). The authors review the behavior of the actinides when complexed with various organic chelating ligands, such as the $\beta$-diketones. This article again indicates the contribution that fluorination plays in the volatility of these compounds, and in particular with regard to complexes of the type UO$_2$(acetylacetonate)$_2$L. It is at this point in that article that it is indicated that the monodentate ligands (L) begin to come off between 83° and 170° C., followed by decomposition of the complex, even though ligands containing nitrogen donor atoms are said to result in decomposition temperatures that are much higher. Again, no direct discussion of volatility is contained in this portion of the Casellato et al article, which goes on to discuss the relationship between ligand selection and shifts in the absorption spectra of the molecule.

The effects of chelate and ligand substitution on the IR spectra is also discussed by Haigh and Thornton in "Ligand Substitution Effects in Uranyl $\beta$-ketoenolates," Chemical Abstracts 75, 55935n, and a further discussion of the effect of fluorine substitution for hydrogen on volatility is made by Swain et al in "Volatile Chelates of Quadrivalent Actinides." Inorganic Chemistry, Vol. 9, No. 7, Pages 1766-9 (1970) which relates to tetravalent uranium compounds, the most volatile of which is U(CH$_3$COCHCOCF$_3$)$_4$, a compound which the author states to be "... too unstable for any practical use."

There is also an article by Bloor et al (Canadian Journal of Chemistry, 42, 2201–2208) which teaches the existance of a compound described as uranyl phthalocyanine, which is said to be sublimable under a vacuum "below 0.01 mm pressure at 400°–450° C."

Finally, in a series of articles by Levy et al and Taylor et al, J. C. S. Dalton, 1628–1640 (1977), the authors discuss their studies of UO$_2$ (hfacac)$_2$ trimethylphosphate. In particular, they studied the thermal effects upon this complex, and concluded that their findings concerning the crystal structures of this compound indicates that polymorphism occurs on heating. It is noted that the boiling point of trimethylphosphate is greater than 190° C. More significantly, however, these articles include no discussion of the specific volatilies or stabilities of these complexes, and these articles do not teach that they or any other related types of complexes would possess the properties of the compounds of the present invention. In fact, quite unexpectedly in view of the disclosures in this series of articles, the applicants have discovered that the trimethylphosphate compound disclosed therein has a higher vapor pressure and volatility than one would expect therefrom, and furthermore that it would be a useful compound in processes such as those discussed herein and disclosed in co-pending application Ser. No. 865,963.

None of these articles thus teach the specific uranyl compounds which are claimed as constituting the present invention. Beyond their mere failure to teach or suggest these compounds, however, stands the fact that there references demonstrate a state of the art in which no uranyl compounds of this nature are shown which have significant volatilities at relatively low temperatures. Lack of any teaching of such compounds, when coupled with the desire to attain uranyl-containing compounds having such properties, is significant proof of the patentable nature of the particular compounds invented by the applicants. It is in this regard that reference is made to co-pending application Ser. No. 865,963, which application claims the use of the present compounds in a process for the separation of isotopes therewith.

There are, however, other uses for these compounds which also require that they be volatile uranyl compounds, such as in the separation of heavy metals by either gas chromatography or fractional sublimation. Such separations are important in mineral treatments and in reprocessing spent nuclear fuels, etc., in which uranium (present as uranyl ion) is to be separated from other rare earth metal ions, actinide metal ions, or other metal ions.

SUMMARY OF THE INVENTION

In accordance with the present invention compositions of matter comprising relatively volatile uranyl ion containing compounds have now been discovered having the general formula $UO_2AA'L_n$, n being either 0 or 1, and A and A' comprising anions whose conjugate acids have boiling points less than about 200° C. and $pK_a$ values of 4.8 or lower, and in which L is a neutral ligand having a boiling point of less than about 190° C. and an equilibrium constant for the exchange reaction with tetrahydrofuran ranging from about $10^{-3}$ to $10^3$, and wherein A, A' and L combine to satisfy five or six coordination sites of said uranium atom. In a preferred embodiment of the present invention both the anions A and A' will comprise the same anion, and in any event these anions will preferably be monovalent.

In another embodiment of the present invention the anions A and A' can be monodentate or polydentate, but preferably they will be bidentate.

In another embodiment of the present invention the anions A and A' will preferably be highly fluorinated, and most preferably will be $(CF_3CO)_2CH$ or will be completely fluorinated.

The composition of matter of the present invention will preferably have a vapor pressure of at least about 0.1 mm at a temperature of less than about 150° C.

In a preferred embodiment of the present invention both of the anions A and A' will comprise the hexafluoroacetylacetonate anion, and preferably the neutral ligand L will comprise isopropanol, ethanol, isobutanol, tert-butanol, ethylacetate, n-propanol, methanol, tetrahydrofuran, acetone, or dimethylformamide, and most preferably tetrahydrofuran.

In accordance with another aspect of the present invention, another group of relatively volatile uranyl compounds have also been found, having the general formula $UO_2AL_n$, n in this case being from 0 to 5, A in this case comprising a divalent anion whose conjugate acid again has a boiling point of less than about 200° C. and a $pK_a$ value of 4.8 or lower, and L is again a neutral ligand having a boiling point of less than about 190° C. and an equilibrium constant for the exchange reaction with tetrahydrofuran ranging from about $10^{-3}$ to $10^3$, and wherein A and L combine to satisfy five or six coordination sites of the uranium atom.

BRIEF DESCRIPTION OF THE DRAWING

The drawing is a three-dimensional graphic representation of the selection of the compounds of the present invention in accordance with the various criteria required for each portion thereof.

DETAILED DESCRIPTION

The uranyl ion containing compounds of the present invention must contain anions having a total net charge of $-2$ so that a neutral complex is formed. Furthermore, these compounds include anions and/or ligands which occupy all of the available sites in the first coordination shell of the uranyl ion in order to minimize the intermolecular electrostatic attraction between one uranyl ion and the anions or ligands surrounding another uranyl ion. As for the anions themselves, they may be monodentate or polydentate, and those which are polydentate will form a chelation ring around a portion of the uranyl ion.

The anions of the present invention are selected so as to effectively enhance the Lewis acidity of the complexed uranyl ion. This is best accomplished by employing electronegative elements such as fluorine in connection with these anions to inductively withdraw electron density from the uranyl ion leading to the formation of more ionic bonds. Thus in cases where a neutral ligand is employed, such as where a pair of bidentate anions occupy four of the available sites in the first coordination shell of the uranyl ion, the ability of the uranyl ion to bond with strong Lewis bases such as those containing oxygen, nitrogen and fluorine atoms is increased. These bases are the neutral ligands L referred to above, and there is of course a reciprocal interaction between the ability of the uranyl ion to combine with the anions and the neutral ligand or base L.

In the case of the anions A and A' in the compounds of this invention their ability to stabilize the complexes of the present invention is directly related to the acidity of their conjugate acids, which can be measured by their acid dissociation constants in water. Furthermore, these conjugate acids must themselves have a minimum volatility so as to boil, at pressures of 1 atmosphere, at temperatures below about 200° C. This is therefore one critical element in the selection of the compounds of this invention having sufficient volatility and stability to be useful for processes such as the isotope separation processes mentioned above.

As for the acidity of these conjugate acids, in order to be useful in the compositions of the present invention, and in forming such volatile complexes, it has also been found that these conjugate acids must have $pK_a$ values of 4.8 or less. That is, these acids must be about at least as strong as trifluoroacetylacetone, which has a $pK_a$ value of about 4.7.

It is next noted that when polydentate anions are employed so as to form a chelation ring around part of the uranyl ion, it is necessary to employ anions such that these chelation rings will not open and bridge at the increased temperatures at which these compounds may be intended to be used, such as above about 50° C., preferably above about 150° C. If these rings were to open and bridge with adjacent uranyl ions at lower temperatures, then there would be a concomitant severe reduction in volatility. It is thus highly preferred that these anions have an atomic framework with a minimum length corresponding to that of the diketonate unit so as to minimize the attack of various basic components in solution on the uranium atom by a frontal approach of the displacing reagent, and so to form relatively unstrained chelate rings. Thus, rings containing 5 and 6 or more members will be much less strained than those with 3 or 4 members and will therefore be less likely to open and bridge to other uranyl ions. Thus, small inorganic chelating ions like nitrate or perchlorate ions would not be suitable candidates for the anionic reagents in the compounds of the present invention.

Preferable anions for use in connection with the compounds of the present invention will thus include, in addition to the hexafluoroacetylacetonate anion discussed above, trifluoroacetylacetonate ($CF_3OCHCOCH_3$) 3,trifluoromethyl)-1,1,1,5,5,5-hexafluoroacetylacetonate (($CF_3CO)_2CCF_3$), 3-trifluoroacetyl-1,1,1,5,5,5-hexafluoro-2,4-pentanedione (($CF_3CO)_3C$), 3-fluoro-1,1,1,5,5,5-hexafluoroacetylacetonate ($CF_3CO)_2CF$), 1,1,1,2,2, 3,3,7,7,7-decafluoro-4,6-heptanedionate (CF₃COCHCOC₃F₇), as well as fluorinated tropolonates, such as

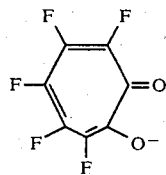

In the case where a neutral ligand L is present in the above formulas, i.e. such as where a pair of bidentate anions occupy 4 of the coordination sites of the uranyl ion, the ligand L must also meet a series of criteria. Reference is again made in this regard to the drawing.

Firstly, it is required that these ligands L also be sufficiently volatile so as to boil, at 1 atmosphere pressure, at temperatures below 190° C.

Secondly, the other key requirement with respect to the neutral ligands L is that they must exceed a minimum basicity to insure that they are a strong electron donor, so as to form a coordinate covalent bond with the uranyl ion. On the other hand, they cannot be too basic so as to reduce the ability of the uranyl ion to interact with the chelating anions discussed above. This required basicity of these ligands L may thus be defined in terms of the molecule UO₂(hfacac)₂.THF. That is, the neutral ligand L will have a basicity measured by the equilibrium constant for the following reaction:

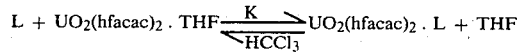

The neutral ligands L of the present invention will yield K's varying from about $10^{-3}$ to $10^3$ therein. K in this case is measured in an anhydrous solvent such as benzene, methylene chloride or chloroform.

Preferable neutral ligands for use in connection with the compounds of the present invention will thus include, in addition to the tetrahydrofuran, isopropanol, ethanol, isobutanol, tert-butanol, ethylacetate, n-propanol, methanol, acetone and dimethylformamide noted above, compounds including pyridine, cyclopentanone, dimethylsulfoxide, acrylonitrile, acetonitrile, tetrahydrothiophene, ethyl ether, and 1,4 dioxane. It is again noted, however, that the use of certain ligands such as acrylonitrile, which do not greatly exceed the minimum basicity requirement set forth above, will necessitate their use in conjunction with an anion(s) whose conjugate acid has an acidity which is considerably greater than the minimum acidity requirement set forth above, since complexes with these ligands are difficult to stabilize unless the Lewis acidity of the uranyl ion is relatively high.

It has also been discovered by George Kramer and others that another class of relatively volatile uranyl compounds having the same general formula set forth above can be prepared even though the neutral ligand L has a boiling point of greater than about 200° C. In that invention, however, it has been found that the ligand L then also requires an equilibrium constant for the exchange reaction with tetrahydrofuran of greater than about $10^3$, and furthermore the ligand L must also be a dipolar species of such compounds. In that case, more strongly basic ligands such as triethylphosphine oxide or triaminophosphine oxide are required. This invention will, however, be the subject of a separate patent application of these inventors which will be prepared and filed shortly.

The basic criteria set forth above can be illustrated as shown in the drawing. In this case a three dimensional axis is established in which the required boiling points for the conjugate acids of the anions (HA or HA') and for the neutral ligand L is shown (thus defining a plane represented by points A, B, C and D in the case of the anions, and a separate plane displaced therefrom but not specifically designated by any points in the drawing, in the case of the ligand). In addition, also shown are the relative basicities of the neutral ligands (bounded by the points E and H or G and F) and the acidities of the conjugate acids of the anions ($pK_a$ being greater than 4.8, which is represented by points B, D, F and G). If all of these criteria are met, then the resultant compounds will fall within the volume defined in the three-dimensional space in front of the plane defined by points B, D, F and G (as shown by the arrows in the drawing). This area as shown in the drawing, thus defining the specific volatile uranyl compounds of this invention.

PREFERRED EMBODIMENT

In the above-noted formula UO₂AA'L$_n$ where the anions A and A' both comprise hexafluoroacetylacetonate anions, and the neutral ligand L comprises a ligand such as isopropanol, ethanol, isobutanol, tert-butanol, ethylacetate, n-propanol, methanol, tetrahydrofuran, acetone, or dimethylformamide, a most preferred composition of matter of the present invention will be obtained.

The vapor pressures for these compounds will be in the range of from about 0.1 to 10 mm when the temperature is in the range of from about 30° to 150° C. In addition, these compositions, having the formula UO₂(hfacac)₂.L, will have no absorption in the infrared region 900–975 cm$^{-1}$ overlapping the UO₂ asymmetric stretch, which can thus be isotope selectively excited with CO₂ laser light.

All of these preferred compositions will sublime intact at temperatures less than about 100° C., and will satisfy the infrared criterion discussed above. Details of the preparation and characterization of these preferred compounds are presented below.

In these preferred compositions of the present invention there is an infrared "window" of the A(hfacac) and L components which allows for irradiation by a CO₂-laser of the UO₂ moiety. In contrast to all previously described uranyl compounds, these have vapor pressures of at least $10^{-1}$ torr at 130° C.

These preferred compositions may be prepared in the manner described below. In the following preparations, the compound UO₂(hfacac)₂.THF will be the case described. Exactly the same procedure will hold to prepare the other preferred compounds, substituting t-butanol, n-propanol, dimethylformamide, ethylacetate, isopropanol, ethanol, isobutanol, methanol and acetone for the THF. Once any of these compounds is prepared, any other of them may also be prepared from it by the process of ligand exchange, that is, by treating the first composition with an excess (greater than about 50/1 mole ratio) of the ligand to be substituted, and evaporating off the excess ligand and replaced ligand.

Three different methods to prepare UO₂(hfacac)₂.THF have been found to work, and are discussed below.

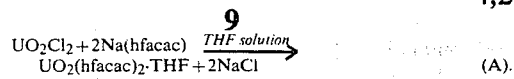

(A)

Anhydrous uranyl chloride is combined with about 2 mole equivalents of sodium hexafluoroacetylacetonate dissolved in tetrahydrofuran which functions as the solvent and as the neutral ligand.

A solvent, THF, in an amount of at least 1 mole is used for each mole of uranyl chloride. More than one mole may be used to increase dissolution.

The uranyl chloride concentration in the solvent may vary from 0.1 to 14 moles/liter. A preferred concentration range is between 0.1 and 3 moles/liter.

The reaction may be refluxed at the boiling point of THF for a period of time to increase the rate of the reaction (less than 24 hours).

The desired product formed is soluble in the solvent and the product and solvent are isolatable by filtration from the sodium chloride which is insoluble in the solution. The excess solvent is evaporated (under nitrogen) leaving the product.

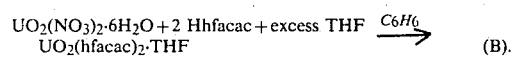

(B)

A uranyl salt such as uranyl nitrate is dissolved in a sufficient amount of water at ambient temperatures. The pH should be maintained between 0 and 7 and may be adjusted by the addition of inorganic acids like HCl or $HNO_3$. The concentration of the uranyl salt may range between 0.001 to 10.0 moles/liter.

In a separatory funnel, this solution is added to a solution of benzene containing at least two mole equivalents of hexfluoroacetylacetone and at least one mole equivalent of the neutral ligand, THF. A volume of benzene approximately equal to the volume of water is used. After shaking the liquids and separating off the lower aqueous phase, which removes most of the water and other coproducts, the resulting benzene solution which contains the desired product is dried over anhydrous sodium sulfate. The sodium sulfate is removed and the benzene solution is evaporated leaving the product. This is to say, the solvent may be removed by conventional vacuum distillation at ambient conditions or by stripping with a flowing nitrogen stream. The final product should preferably be stored in an inert atmosphere and shielded from light.

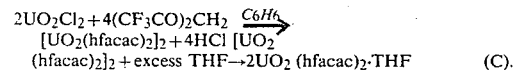

(C)

Uncomplexed uranyl hexafluoroacetylacetonate is first prepared by reacting uranyl chloride with at least two moles of the diketone in refluxing benzene. These operations are preferably conducted in the absence of air.

The uranyl chloride may be in a slurry whose concentration ranges from 0.001 to 10 moles/liter and it is reacted with at least two mole equivalents of the diketone. HCl generated in the reaction is removed. The product, $[UO_2(hfacac)_2]_2$ is recovered after evaporating the benzene solvent. It is easily converted into the THF complex by being dissolved in at least 1 mole equivalent of the solvent, and it may be recovered as in Example A.

EXAMPLE 1: Preparation of $UO_2(hfacac).THF$ by Method A

Anhydrous uranyl chloride (3.4 g, 10 millimol) is dissolved in 25 ml of THF, and to this solution is added 25 ml of a solution of 4.6 g (20 millimol) sodium salt of hexafluoroacetylacetone. The reaction is refluxed an hour, the sodium chloride is filtered off and the filtrate evaporated to yeild about 7.5 g yellow solid, mp 85°–86° C.

EXAMPLE 2: Preparation of $UO_2$ (hfacac).L by Method B 5.0 g of uranyl nitrate (10 millimol) is dissolved in 100 ml water maintained at pH 3. In a separatory funnel this solution is added to 100 ml of a benzene solution containing 4.2 g hexafluoroacetylacetone and 5 ml of THF. After shaking the liquids and separating off the lower aqueous phase, the benzene solution resulting is dried over anhydrous sodium sulfate and evaporated, leaving 3.0 g yellow solid, mp 90° C.

EXAMPLE 3: Prepration of $UO_2$ (hfacac).L by Method C

Uranyl hexafluoroacetylacetonate is prepared by refluxing uranyl chloride (3.4 g, 10 millimoles) in benzene (50 ml) with hexafluoroacetylacetone (8.3 g, 40 millimoles). The product is soluble in benzene and easily recrystallized from it. When dissolved in THF and evaporated to dryness, a yellow solid, mp 85°–97° C. remains.

All of the crude products obtained above were essentially identical. For the purposes envisioned for the compositions, they could be purified by one of two general methods, either by vacuum sublimation at about 0.1 torr (temperatures of 50°–70° C.), or by recrystallization from benzene or hydrocarbons such as hexane. In both cases nice yellow crystals were obtained, melting point, 92°–92.5° C.

Elemental analysis for $UO_2(hfacac)_2.THF$, (MW 756) gave the following results:

|   | Calculated | Found |
|---|---|---|
| C | 22.2 | 22.5 |
| H | 1.3 | 1.5 |
| F | 30.1 | 28.6 |

Mol wt by mass spectrometry is 756 and by cryoscopy in benzene is 752.

On repeated sublimations, the composition of the compound remained constant. That is, the neutral ligand remains bonded to the $UO_2^{+2}$ group during and after vaporization (unlike other $\beta$-diketonates of $UO_2^{+2}$ as described in Casellato, referred to above).

The compositions described above were characterized (in addition to elemental analyses) by mass spectrometry, infrared and ultraviolet spectroscopy, and nmr spectroscopy. The melting points and sublimation temperatures, as well as the asymmetric stretching band in the infrared are summarized in Table I.

TABLE I

Summary of the Complexes
$UO_2(hfacac)_2 \cdot L$

| L | mp(°C.) | Sublimation Temperature* | $UO_2^{+2}$ Infrared Absorption (cm$^{-1}$, benzene soln) |
|---|---|---|---|
| THF | 92–92.8° | 70° C. | 950 |
| CH$_3$OH | 117–120° | 50° | 947 |
| C$_2$H$_5$OH | 110–115° | 40° | 947 |
| i-C$_3$H$_7$OH | 128–120° | 45° | 948 |
| i-C$_4$H$_9$OH | 51–55° | 80 | 948 |
| t-C$_4$H$_9$OH | 105–117° | 60° | 948 |
| CH$_3$COCH$_3$ | 89–92° | 55° | 948 |
| ethylacetate | 58–63° | 100° | 948 |

What is claimed is:

1. A composition of matter having the formula:

$UO_2AA'L_n$ n being 0 or 1, wherein A and A' comprise anions whose conjugate acids have boiling points of less than about 200° C. and pK$_a$ values of 4.8 or lower, L comprises a neutral ligand having a boiling point of less than about 190° C. and an equilibrium constant for exchange with tetrahydrofuran ranging from about $10^{-3}$ to $10^3$, and A, A' and L combine to satisfy five or six coordination sites of said uranium atom.

2. The composition of matter of claim 1 having a vapor pressure of at least about 0.1 mm at a temperature of less than about 150° C.

3. The composition of matter of claim 1 wherein A and A' comprise the same anion.

4. The composition of matter of claim 1 wherein said anions have an atomic framework having a minimum length corresponding to that of the diketonate unit.

5. The composition of matter of claim 1 wherein n equals 1, and L comprises a neutral ligand selected from the group consisting of isopropanol, ethanol, isobutanol, tert-butanol, ethylacetate, n-propanol, methanol, tetrahydrofuran, acetone, dimethylformamide, and dimethylsulfoxide.

6. The composition of matter of claim 5 wherein said anion comprises hexafluoroacetylacetonate.

7. The composition of matter of claim 1 wherein both A and A' comprise anions which are monovalent.

8. The composition of matter of claim 1 wherein both A and A' comprise anions which are polydentate.

9. The composition of matter of claim 1 wherein said anions are bidentate.

10. The composition of matter of claim 1 wherein n equals 1 and said ligand L is monodentate.

11. The composition of matter having the formula:

$UO_2AL_n$ n being from 0 to 5, wherein A comprises a divalent anion whose conjugate acid has a boiling point of less than about 200° C. and a pK$_a$ value of 4.8 or lower, L comprises a neutral ligand having a boiling point of less than about 190° C. and an equilibrium constant for dissociation substitution compared to that of tetrahydrofuran ranging from about $10^{-3}$ to $10^3$, and A and L combine to satisfy five or six coordination site of said uranium atom.

12. The composition of matter of claim 11 having a vapor pressure of at least about 0.1 mm at a temperature of less than about 150° C.

13. The composition of matter of claim 11 wherein n equals 1, and L comprises a neutral ligand selected from the group consisting of isopropanol, ethanol, isobutanol, tert-butanol, ethylacetate, n-propanol, methanol, tetrahydrofuran, acetone, dimethylformamide, and dimethylsulfoxide.

14. The composition of matter of claim 11 wherein n equals 2 and said ligands L are bidentate.

* * * * *